United States Patent

Van Der Puy

[11] Patent Number: 5,998,671
[45] Date of Patent: Dec. 7, 1999

[54] FLUORINATED KETONES AND METHOD FOR MAKING SAME

[75] Inventor: Michael Van Der Puy, Amherst, N.Y.

[73] Assignee: Alliedsignal Inc., Morristown, N.J.

[21] Appl. No.: 09/079,606

[22] Filed: May 15, 1998

[51] Int. Cl.[6] .................................................. C07C 45/80
[52] U.S. Cl. ............................ 568/411; 568/403; 568/407
[58] Field of Search ..................................... 568/364, 407, 568/411, 403, 419

[56] References Cited

U.S. PATENT DOCUMENTS

| | | | |
|---|---|---|---|
| 3,091,643 | 5/1963 | Wiley | 260/595 |
| 4,172,851 | 10/1979 | Childs | 260/593 H |

OTHER PUBLICATIONS

"Preparation of Perfluoroalkyl Ketones", A. Nakahara. Y. Izeki, J. Nakajima, Jpn. Kokai Tokyo Koho JP 01,226,846, CA 112 [89,226,846], 1990.

C. G. Krespan and W. J. Middleton, Fluorine Chem Rev., 1, (1967) 145.

"Reactions of Perfluorinated Propylmagnesium Iodide", A. L. Henne and W. C. Francis, J. Am. Chem. Soc., 75(1953) 992.

"Trifluoroacetic Acid: Sources Of Trifluoromethyl Groups Access To Derivatives Of Triflic Acid", J. R. Desmers, G. Forat, J.M. Mas, V. Pevere, S. Ratton, N. Roques, J. Russell, L. Saint–Jalmes, Abstract O(3) C–5, 15th International Symposium of Fluorine Chemistry, Vancouver, Canada, Aug. 1997.

"Formation of Symmetrical Ketones From Self–Condensations of Anhydrides by Boron Fluoride", E. H. Man and C. R. Hauser, J. Am. Chem. Soc., 72, (1950), 3294.

Primary Examiner—Shailendra Kumar
Assistant Examiner—S. Padmanabhan
Attorney, Agent, or Firm—Colleen D. Szuch; Marie Collazo

[57] ABSTRACT

A method for the preparation of a fluorinated ketone of the formula:

$$R_1CF_2\underset{\underset{O}{\|}}{C}CF_2R_2$$

where $R_1$ and $R_2$ are independently fluorine, alkyl of from about 1 to about 8 carbon atoms, fluoroalkyl of from about 1 to about 8 carbon atoms, or $$R_3CF_2\underset{\underset{O}{\|}}{C}CF_2(R_4)_{\overline{n}}\text{\textemdash}$$

where $R_3$ and $R_4$ are independently fluorine, alkyl of from about 1 to about 8 carbon atoms, or fluoroalkyl of from about 1 to about 8 carbon atoms and n is 0 or 1. The method includes heating an anhydride of the formula:

$$R_1CF_2\underset{\underset{O}{\|}}{C}O\underset{\underset{O}{\|}}{C}CF_2R_2$$

with a catalyst including a cationic salt of a fluorocarboxylic acid or an alkali metal fluoride to obtain the fluorinated ketone.

14 Claims, No Drawings

FLUORINATED KETONES AND METHOD FOR MAKING SAME

BACKGROUND OF THE INVENTION

Fluorinated ketones are useful, reactive chemical intermediates, e.g. to make condensation type polymers, e.g. polyamides, polyimides and polyesters suitable for coatings, electronics and high performance polymers. The ketones can also be reduced to alcohols which also have utility as intermediates. Hexafluoroacetone, for example, is widely used commercially in the manufacture of fluorinated aromatic polyesters, polyamides, and polyimides (see W. K. Appel, B. A. Blech, and M. Stobbe in "Organofluorine Chemistry Principles and Commercial Applications", p 413, Plenum Press, New York, 1993).

Several synthetic methods for perfluorinated ketones have been reported. Few, if any, however, appear to be suitable for all members of the family of perfluoroketones, $R_fC(O)R_f$, where $R_f$ is a perfluoroalkyl group. For example, the more useful methods for preparing hexafluoroacetone, such as the halogen exchange of hexachloroacetone and the isomerization of hexafluoropropene oxide (for a review of hexafluoroacetone, see C. G. Krespan and W. J. Middleton, *Fluorine Chem. Rev*, 1 (1967) 145) do not work or do not give pure materials when applied to higher homologs in the series. For this reason other methods have been necessary for these higher molecular weight ketones. Perfluoro-3-pentanone has been prepared by the cesium fluoride catalyzed reaction of perfluoropropionyl fluoride with tetrafluoroethylene (A. Nakahara, Y. Izeki, and J. Nakajima, Jpn. Kokai Tokyo Koho JP 01, 226, 846; CA 112:P118260u). Perfluoro-4-heptanone has been prepared by the reaction of sodium ethoxide with ethyl perfluorobutyrate (D. W. Wiley, U.S. Pat. No. 3,091,463 Mar. 28, 1963). According to this patent (Wiley's method), one mole of an alkali metal alkoxide is treated with 2 moles of an ester of a fluorinated acid having not less than three carbon atoms in the acid portion of the ester. Although the yield was good, reaction times were long, e.g. several days and involved complex product isolation and dehydration procedures. Perfluoro-4-heptanone has also been prepared in 20% yield by the action of heptafluoromagnesium iodide on ethyl heptafluorobutyrate (A. L. Henne and W. C. Frances, *J. Am. Chem. Soc.*, 75 (1953) 992).

The decarboxylation of salts of haloacetic acids has been used as a means to generate trihalomethide ($CF_3^-$) ions. For example, salts of trifluoroacetic acid, e.g., $CF_3COOK$, were heated in a solvent and the $CF_3^-$ anion generated was reacted with appropriate electrophiles such as $SO_2$ to generate trifluoromethylated compounds, such as $CF_3SO_2K$ (J. R. Desmers, G. Forat, V. Pevere, S. Ratton, N. Rogues, J. Russell, and L. Saint-Jalmes, Abstract O(3) C-5, $15^{th}$ International Symposium on Fluorine Chemistry, Vancouver, Canada, August, 1997).

In the case of non-fluorinated anhydrides, the transformation of anhydrides to ketones has found limited use in the preparation of symmetrical ketones (E. H. Man and C. R. Hauser, *J. Am. Chem. Soc.*, 72, (1950), 3294). The catalyst is boron trifluoride (used in large quantity to form a saturated solution), and appears to be limited to anhydrides which have a hydrogen on the carbon adjacent to the carbonyl carbon. In these reactions decarboxylation does not occur until the initially formed products (anhydrides in which one or more hydrogens have been replaced by RC(O) groups) are hydrolyzed. H. Meerwein and D. Vossen, (*J. Prakt. Chem.*, 141 (1934) 149) indicate for the conversion of acetic anhydride to 2,4-pentanedione, for example, the stoichiometry is: $5\ CH_3C(O)OC(O)CH_3+H_2O$ (during work-up) $\rightarrow 2CH_3C(O)CH_2C(O)CH_3+4CH_3COOH+2CO_2$.

DESCRIPTION OF THE INVENTION

In the process of the present invention, a fluorinated acid anhydride is treated with a catalyst at a reaction temperature suitable to convert the anhydride to a ketone, with the expulsion of carbon dioxide, according to Equation 1:

$$R_xC(O)OC(O)R_y \rightarrow R_xC(O)R_y + CO_2 \qquad \text{Equation 1}$$

This reaction is distinct from that described by Man et. al. above, in that the decarboxylation occurs without hydrolysis. $R_x$ is generally $R_1CF_2$— and Ry is $R_2CF_2$—. $R_1$ and $R_2$ are described below.

More particularly, the invention includes a method for the preparation of a fluorinated ketone of the formula:

where $R_1$ and $R_2$ are independently fluorine, alkyl of from about 1 to about 8 carbon atoms, fluoroalkyl of from about 1 to about 8 carbon atoms, or

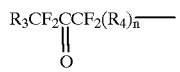

where $R_3$ and $R_4$ are independently fluorine, alkyl of from about 1 to about 8 carbon atoms, or fluoroalkyl of from about 1 to about 8 carbon atoms and n is 0 or 1. The method comprises heating an anhydride of the formula:

with a catalyst comprising a cationic salt of a fluorocarboxylic acid or an alkali metal fluoride to obtain the fluorinated ketone where $R_1$ and $R_2$ are as defined above.

The anhydride used as the starting material, in accordance with the present invention, must be at least partially fluorinated, especially on the carbon atoms adjacent to the anhydride carbon atoms. Anhydrides which are not fluorinated on the carbons adjacent to the anhydride carbons will not react in accordance with the method of the invention. Many of such anhydrides are commercially available but in any case can be made by dehydration of the corresponding $C_x$–$C_{x+1}$ dicarboxylic acids. Such dehydration desirably takes place with a second non-fluorinated anhydride. For example, trifluoroacetic anhydride can be prepared from trifluoroacetic acid by dehydration with a second anhydride, such as dichloroacetic anhydride. The reaction produces trifluoroacetic anhydride and dichloroacetic acid which is recycled. Many starting dicarboxylic acids are commercially available and are readily made by electrochemical fluorination of the corresponding hydrocarbon acid fluorides. The anhydride is usually a monoanhydride but may contain more than one anhydride structure provided that the anhydrides are separated from each other by at least two, and preferably at least about four —$CF_2$— groups.

The starting anhydride may, for example be selected from: $CF_3CF_2CF_2C(O)OC(O)CF_2CF_2CF_3$, $CHF_2CF_2C(O)OC(O)CF_2CF_2H$, $CF_3CF_2C(O)OC(O)CF_3$, $CH_2FCF_2CF_2CF_2C(O)$ OC(O)CF$_3$, CF$_3$C(O)OC(O)CF$_3$, CF$_3$CF$_2$CF$_2$C(O)OC(O) CF$_2$CF$_2$CH$_3$, and CF$_3$CF$_2$CF$_2$C(O)OC(O)CF$_2$CF$_2$CF$_2$C (O)OC(O)CF$_2$CF$_2$CF$_3$. In the simplest case, R$_x$ and R$_y$ in Equation 1 are perfluoromethyl groups. The reaction described is then the conversion of trifluoroacetic anhydride to hexafluoroacetone.

A catalyst is required for the method of the invention. The catalyst preferably comprises an ether soluble cationic salt of fluorocarboxylic acid such as a metal fluorocarboxylate. The cation of the ether soluble cationic salt of fluorocarboxylic acid is a group IA metal ion, group IIA metal ion, group IB metal ion or trimethylsilyl. Preferred catalysts may be selected from cesium trifluoroacetate, potassium trifluoroacetate, sodium trifluoroacetate, rubidium trifluoroacetate, silver trifluoroacetate, cesium perfluorooctanoate, potassium heptafluorobutyrate, cesium 7H-perfluoroheptanoate, and potassium 2,2,3,3-tetrafluoropropionate. More preferred effective catalysts are alkali metal salts (especially cesium and potassium salts) of perfluorinated carboxylic acids. Alkali metal fluorides will produce metal carboxylate by reaction with anhydride; thus, other suitable catalysts are alkali metal fluorides such as cesium, potassium and sodium fluorides. Catalysts as described above are generally commercially available.

The catalysts appear to function as follows. First, the perfluorocarboxylate anion of the metal salt undergoes a decarboxylation to produce a perfluoroalkyl anion. Next, the perfluoroalkyl anion reacts with the anhydride to form a ketone and another perfluorocarboxylate anion, which then begins a new catalytic cycle (Equations 2a and 2b). The net reaction is then given by Equation 1.

R$_f$COO$^-$M$^+$→(R$_f^-$)M$^+$+CO$_2$                Equation 2a

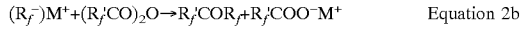
(R$_f^-$)M$^+$+(R$_f'$CO)$_2$O→R$_f'$COR$_f$+R$_f'$COO$^-$M$^+$                Equation 2b It is apparent that only a small amount of the metal carboxylate needs to be present, and furthermore, when the ratio of anhydride to catalyst is large, R$_f$ in the catalyst need not be the same as R$_f'$ in the anhydride, since the ratio of product ketones containing one or two R$_f$ groups will be small compared to the desired ketone containing two R$_f'$ groups. This is useful from a practical standpoint since metal trifluoroacetates are readily available; whereas, metal salts of the higher members of the series are not. By using stoichiometric amounts of the catalyst, relative to the anhydride, mixed perfluoroketones, i.e., R$_f$COR$_f'$ can be obtained when R$_f$ in the catalyst is not the same as R$_f'$ in the anhydride. Thus, for example, ketones of the type R$_f'$COCF$_3$ can be obtained by reacting CF$_3$COOM with (R$_f'$CO)$_2$O.

Typical reaction temperatures range from about 160 to 240° C., depending on the catalyst used. In the case of cesium trifluoroacetate, the onset of reaction will be in the lower end of this range. Good reaction rates are generally observed at 175 to 190° C. The most preferred range for many reactions is from about 175 to about 185° C. In the case of the lower alkali metal carboxylates (sodium and potassium salts), suitable reaction temperatures tend to be 10–20 degrees higher, but the use of crown ethers (e.g. 18-crown-6) in conjunction with these salts is advantageous, as their use allows the reaction to be run at lower temperatures. Reaction times within the above temperatures range from several minutes to a few hours, e.g. from about 5 minutes to about 5 hours. Preferably, when a cesium carboxylate catalyst is used in conjunction with an ether solvent, reaction times can be kept below about one hour and more preferably below about 30 minutes.

In the method, the heating preferably occurs in a non-reactive solvent. The solvent may, for example comprise sulfolane or an ether. Any solvent that is used must not only be stable to the reagents and reaction conditions used but should also be substantially anhydrous to avoid hydrolysis of the anhydride and non-acidic to avoid formation of R$_f$H compounds. When the solvent comprises an ether, it may, for example, be an alkyl polyether, a crown ether, a dialkyl ether, a cyclic ether or mixtures thereof. More specifically, the ether may comprise dimethoxyethane, 2-methoxyethyl ether(diglyme), di(ethylene glycol)diethyl ether, triethylene glycol dimethyl ether, tetraethylene glycol dimethyl ether, dioxane, or 18-crown-6 ether. In addition to ether, the solvent may include a hydrofluorocarbon or a hydrofluorocarbon ether.

Although the decarboxylation reaction can occur in the absence of a solvent, solvents generally lower the reaction temperature. For example, in the absence of solvent, cesium trifluoroacetate was not an effective catalyst until the reaction temperature was about 230° C. With diglyme as the solvent, a comparable rate was achieved at about 185° C. Similarly, the complex of potassium trifluoroacetate and 18-crown-6 ether was not effective below about 220° C., but in diglyme solution, the rate of reaction was superior at 185° C.

The best commercial solvents evaluated were ether solvents, due primarily to good stability at elevated temperatures in the presence of these reactive starting materials. Dimethylformamide was a comparatively poor solvent, since even after one batch run, a significant amount of non-volatile, dark, water-insoluble material was formed in the reaction.

The products of the reaction, fluorinated ketones, may be liquids or gases. When the anhydride is trifluoroacetic anhydride, the product is gaseous hexafluoroacetone (bp −27° C.). The product can therefore easily be isolated from the relatively non-volatile solvent and unreacted anhydride (bp 39° C.), and separated from by-product CO$_2$ (bp −78°). The liquid remaining in the reaction vessel, containing catalyst, unreacted anhydride, and solvent, may then be re-used in another batch run. Although higher molecular weight perfluorinated acid anhydrides may not be soluble in the preferred ether solvents at room temperature, at the reaction temperature, the reaction mixtures are nearly always homogeneous. When the product mixtures are cooled back to room temperature, the higher molecular weight perfluoroketones often separate as a lower liquid layer. They are thus easily separated from the solvent layer and can then be further purified by e.g. distillation. Although the reaction yields for higher molecular weight ketones with this procedure tend to be lower compared to Wiley's method, the simplicity of this process and short reaction time is in contrast to Wiley's method.

By-products include compounds of the type R$_f$H, which arise by trapping of R$_f^-$ anions with acidic materials which may be present as impurities. These are most commonly the acid corresponding to the anhydride starting material and/or moisture present in the catalyst or solvent. Generally, however, the use of anhydrous, pure reagents can reduce the level of R$_f$H compounds to <2% of the product gas mixture. For anhydrides in which the corresponding R$_f^-$ anion contains more than one carbon, fluoride ion loss can also occur to give a fluorinated olefin. Thus, for example, CF$_3$CF=CF$_2$ is a by-product when (CF$_3$CF$_2$CF$_2$CO)$_2$O is used as the anhydride. Another by-product is the corresponding acid fluoride, R$_f$COF. This material is also believed to arise from decomposition of R$_f^-$ anions. If for example, a fluorinated olefin is produced, the fluoride ion which also results can react with the anhydride to form the acid fluoride and a perfluorocarboxylate anion. When the $R_f^-$ ion is trifluoromethide ion, it can also decompose to give fluoride ion and difluorocarbene. Thus it is important to minimize the formation of fluoride in the process in order to maximize the yield of the desired perfluoroketone. (It can be appreciated, however, that metal fluorides will produce metal carboxylates by reaction with the anhydride and thus indirectly can be used as a catalyst if the mole ratio of metal fluoride to anhydride is small, since the true catalyst is produced in this reaction). One approach is to maintain a high concentration of anhydride so that $R_f^-$ anions are immediately trapped by the anhydride thereby minimizing decomposition to fluoride ion. In a batch process, this can easily be controlled unless the reaction is run to high conversions. If the reaction is run to high conversions of the anhydride, the concentration of anhydride will diminish near the end of the reaction to the point where $R_f^-$ ions are no longer trapped effectively. Thus to achieve high selectivities it is necessary to operate at low conversions, preferably in the range of 30–60%. In a continuous process, even lower conversions can be tolerated. In a continuous process, gaseous products are removed continuously while continuously feeding make-up anhydride into the reactor. Thus the concentration of anhydride can be maintained at a high level. It is recommended that the concentration of anhydride be about 10–30 weight percent relative to the weight of solvent, however, to keep the catalyst in solution. This becomes increasingly important as the solubility of catalyst diminishes (as the atomic number of the alkali metal cation decreases). Specific ratios will depend on the combination of reagents employed. They can be determined without excessive experimentation with the aid of the following examples as guidelines.

EXAMPLES

Example 1
Preparation of Hexafluoroacetone from Trifluoroacetic Anhydride in the Absence of Solvent A 450-mL, glass-lined autoclave was charged with 2.7 grams of anhydrous cesium trifluoroacetate and evacuated. Trifluoroacetic anhydride (62.9 grams) was then added and the contents heated. When the temperature reached approximately 230° C., the pressure began to increase without an additional increase in temperature, indicating the approximate temperature for the onset of reaction. Heating was continued for 35 minutes at 230±7° C., during which time the pressure increased from 400 to 620 psig. After cooling the contents to room temperature, the product gases (35.0 grams) were vented slowly. The gases were analyzed at various times during the venting process, and found to contain 1–2% $CHF_3$, 30–35% $CF_3COF$, and the remainder primarily hexafluoroacetone and its hydrates ($CO_2$ was not included in the percentages). The residue in the autoclave consisted of dark solids and liquid.

Example 2
Preparation of Hexafluoroacetone from Trifluoroacetic Anhydride in the Presence of 2-Methoxyethyl Ether In a manner similar to that described in Example 1, 3.6 grams of cesium trifluoroacetate, 19.3 grams of anhydrous 2-methoxyethyl ether, and 63.8 grams of trifluoroacetic anhydride were heated in a glass-lined autoclave. The pressure increased without further increase in temperature at about 180° C. Heating was continued at 177±5° C. for 31 minutes, during which time the pressure increased from 320 to 620 psig. After cooling the contents to 23° C., the pressure in the autoclave was 200 psi. The product gases were analyzed as before and found to contain 4.3% $CHF_3$, 26.0% $CF_3COF$, and 69.3% hexafluoroacetone and its hydrate. Thus, with the use of an ether solvent, similar results were obtained at 177° compared to 230° C. used in Example 1. The residue in the autoclave consisted of a non-viscous liquid, which could be recycled in a second batch run. Thus, after venting the volatiles, the autoclave was recharged with 40.0 grams of trifluoroacetic anhydride, and the contents heated to 179±7° C. for 58 minutes. Analysis of the product gases, not including $CO_2$ indicated 4.7% $CHF_3$, 23.6% $CF_3COF$, and 67.7% hexafluoroacetone and its hydrate.

Comparative Example 3
Reaction of $CF_3COOCs$ With $(CF_3CO)_2O$ in Dimethylformamide In a manner similar to that of Example 2, 1.1 grams of cesium trifluoroacetate, 19.0 grams of anhydrous dimethylformamide, and 63.4 grams of trifluoroacetic anhydride were heated in a glass-lined autoclave to 171±15° C. for 2.5 hours. The pressure increased approximately 250 psi during this heating period without further increasing the temperature. The residue in the autoclave consisted of a black, viscous liquid.

Example 4
Preparation of Perfluoro-4-Heptanone

A 100 mL pressure bottle was charged with 0.339 gram (0.0014 mol) of cesium trifluoroacetate and evacuated. Anhydrous diglyme (4.9 grams) and heptafluorobutyric anhydride (4.2 grams, 0.0102 mol; mole ratio anhydride to cesium salt: 7.3; weight ratio solvent to anhydride=1.17) were then added and the mixture heated to 195–198° C. for 17 minutes. On cooling to room temperature, the product phase separated from the solvent phase. The vapor above the liquid contained some perfluoropropene, $CF_3CF_2CF_2H$, and $CF_3CHFCF_3$, in addition to carbon dioxide. Distillation of the crude liquid provided 0.7 gram (19% yield) of perfluoro-4-heptanone. IR ($cm^{-1}$): 1786.

Example 5
Preparation of Perfluoro-4-Heptanone at Higher Anhydride Concentration.

In a manner similar to that described in Example 3, 0.4 gram of cesium trifluoroacetate, 10.8 grams of diglyme, and 15.9 grams of heptafluorobutyric anhydride (mole ratio anhydride to cesium salt: 24.3; weight ratio solvent to anhydride=0.68) were heated in a 370 mL glass pressure bottle to 189±2° C. for 45 minutes. After cooling to room temperature, the pressure was 41 psi. Distillation of the liquid phases gave 6.0 grams (42% yield of perfluoro-4-heptanone, b.p. 76–78° C. (lit 76° C.; D. W. Wiley, U.S. Pat. No. 3,091,463 Mar. 28, 1963). $^{19}F$ NMR: –81.5 (3F), –118 9 (2F), –126.5 (2F) ppm.

Example 6
Use of $CF_3COOK$ as Catalyst With and Without Crown Ether

A 100 mL glass pressure reactor was charged with 1.02 g potassium trifluoroacetate, 5 mL triglyme, and 4.0 g of trifluoroacetic anhydride and the mixture heated to 195° C. for 30 minutes. After cooling to room temperature (pressure=77 psi), the product gases were vented. Trifluoroacetic anhydride (2.4 g) was charged into the reactor and the contents reheated to 195° for 28 minutes. After cooling, the product gases were analyzed and found to consist of 5.1% $CHF_3$, 13.6% $CF_3COF$, and 69% hexafluoroacetone and its hydrate.

A similar experiment was conducted except that 2.0 grams of 18-crown-6 ether was heated together with 1.0 g CF$_3$COOK, 3.6 g trifluoroacetic anhydride, and 10 mL diglyme. At a reaction temperature of 183–186° C., a similar pressure increase was produced in 45 minutes.

Example 7
Successive Batch Runs as a Model for a Continuous Process

Three successive batch runs were made to simulate a continuous process in which gaseous products (primarily CO$_2$ and hexafluoroacetone are vented continuously through a condenser and pressure control valve (and thence into appropriate isolation vessels such as cold traps) while simultaneously feeding the anhydride under pressure such that the total weight of reactants remains essentially constant. This procedure permits favorable ratios of reactants to be maintained so as to maximize the yield of the desired ketone and at the same time allows the reaction to be conducted at constant and modest pressures of 200 psi or less.

In the following batch run cycles, each cycle represents the conversion of approximately 40% of the trifluoroacetic anhydride present at the beginning of the cycle. The concentration of anhydride oscillates between about 25 weight % to about 15 weight % relative to the total weight of reactants and solvent.

Cycle 1: A glass pressure reactor was charged with 0.43 g. CF$_3$COOCs, 10 mL diglyme, and 2 mL (3 g) of trifluoroacetic anhydride. The contents were heated to 199±3° C. for 31 minutes (the pressure increased 42 psi during this time). The contents were cooled to room temperature, and the product gases (about 1.4 g) were vented and analyzed by gas chromatography.

Cycle 2: To the liquid remaining from Cycle 1 was added 1.5 g trifluoroacetic anhydride and the contents heated to 184±2° C. for 2.5 hours (the pressure increased about 35 psi during this time). Again the contents were cooled and the product gases vented and analyzed.

Cycle 3: To the liquid remaining from Cycle 2 was added 2.2 g trifluoroacetic anhydride and the contents heated to 183±3° C. for 1.5 hours (the pressure increased about 36 psi during this time). The gaseous products were vented and analyzed as before. The results for the three cycles are given in Table 1 (percentages do not include CO$_2$ or anhydride starting material). The liquid remaining in the reactor was a clear, amber solution. The results show that high yields of ketone can be produced reproducibly (the hydrate is believed to arise during manipulation for analysis, and is a minor component, generally <10%, of the total)

TABLE 1

Product distribution from successive batch runs

| Product | Cycle 1 | Cycle 2 | Cycle 3 |
|---|---|---|---|
| CHF$_3$ | 1.8% | 1.4% | 1.5% |
| CF$_3$COF | 3.4% | 2.7% | 1.9% |
| CF$_3$C(O)CF$_3$ + hydrate | 89.9% | 95.2% | 95.7% |
| Other | 4.9% | 0.7% | 0.9% |

Example 8

Example 4 is repeated except that various anhydrides are used as follows: CHF$_2$CF$_2$C(O)OC(O)CF$_2$CF$_2$H; CF$_3$CF$_2$C(O)OC(O)CF$_3$; CH$_2$FCF$_2$CF$_2$CF$_2$C(O)OC(O)CF$_3$; CF$_3$CF$_2$CF$_2$C(O)OC(O)CF$_2$CF$_2$CH$_3$; and CF$_3$CF$_2$CF$_2$C(O)OC(O)CF$_2$CF$_2$CF$_2$CF$_2$C(O)OC(O)CF$_2$CF$_2$CF$_3$ to obtain the corresponding fluorinated ketones.

What is claimed is:

1. A method for the preparation of a fluorinated ketone of the formula:

where R$_1$ and R$_2$ are independently fluorine, alkyl of from about 1 to about 8 carbon atoms, fluoroalkyl of from about 1 to about 8 carbon atoms, or

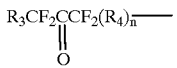

where R$_3$ and R$_4$ are independently fluorine, alkyl of from about 1 to about 8 carbon atoms, or fluoroalkyl of from about 1 to about 8 carbon atoms and n is 0 or 1, said method comprising heating an anhydride of the formula:

with a catalyst comprising a cationic salt of a fluorocarboxylic acid or an alkali metal fluoride to obtain said fluorinated ketone.

2. The method of claim 1 wherein the heating occurs in a non-reactive solvent.

3. The method of claim 2 wherein the solvent comprises sulfolane or an ether.

4. The method of claim 3 wherein the solvent comprises an ether selected from the group consisting of alkyl polyethers, crown ethers, dialkyl ethers and cyclic ethers.

5. The method of claim 2 wherein the non-reactive solvent comprises an ether selected from the group consisting of dimethoxy ethane, 2-methoxyethyl ether, di(ethylene glycol)diethyl ether, triethylene glycol, dimethyl ether, tetraethylene glycol dimethyl ether, dioxane, and 18-crown-6 ether.

6. The method of claim 4 wherein in addition to ether, the solvent comprises a hydrofluorocarbon or a hydrofluorocarbon ether.

7. The method of claim 1 wherein the anhydride is heated to from about 160 to about 240° C.

8. The method of claim 7 wherein the anhydride is heated to from about 175 to about 190° C.

9. The method of claim 1 wherein the catalyst comprises an ether soluble cationic salt of fluorocarboxylic acid.

10. The method of claim 9 wherein the catalyst comprises a metal fluorocarboxylate selected from the group consisting of cesium trifluoroacetate, potassium trifluoroacetate, sodium trifluoroacetate, rubidium trifluoroacetate, silver trifluoroacetate, cesium perfluorooctanoate, potassium heptafluorobutyrate, cesium 7H-perfluoroheptanoate, and potassium 2,2,3,3-tetrafluoropropionate.

11. The method of claim 1 wherein the cation of the ether soluble cationic salt of fluorocarboxylic acid is a group IA metal ion, group IIA metal ion, group IB metal ion or trimethylsilyl.

12. The method of claim 1 wherein the anhydride is selected from the group consisting of CF$_3$CF$_2$CF$_2$C(O)OC(O)CF$_2$CF$_2$CF$_3$, CHF$_2$CF$_2$C(O)OC(O)CF$_2$CF$_2$H, CF$_3$CF$_2$C(O)OC(O)CF$_3$, CH$_2$FCF$_2$CF$_2$CF$_2$C(O)OC(O)CF$_3$, CF$_3$C(O)OC(O)CF$_3$, CF$_3$CF$_2$CF$_2$C(O)OC(O)CF$_2$CF$_2$CH$_3$, and CF$_3$CF$_2$CF$_2$C(O)OC(O)CF$_2$CF$_2$CF$_2$C(O)OC(O)CF$_2$CF$_2$CF$_3$.

13. The method of claim 1 wherein the anhydride is trifluoroacetic anhydride and the ketone is hexafluoroacetone.

14. A method for the preparation of a fluorinated ketone of the formula:

$$R_1CF_2CCF_2R_2$$
$$\underset{O}{\|}$$

where $R_1$ and $R_2$ are independently fluorine, alkyl of from about 1 to about 8 carbon atoms, fluoroalkyl of from about 1 to about 8 carbon atoms, or $$R_3CF_2CCF_2(R_4)_{\overline{n}}\text{—}$$
$$\underset{O}{\|}$$

where $R_3$ and $R_4$ are independently fluorine, alkyl of from about 1 to about 8 carbon atoms, or fluoroalkyl of from about 1 to about 8 carbon atoms and n is 0 or 1, said method comprising heating an anhydride of the formula:

$$R_1CF_2COCCF_2R_2$$
$$\underset{O\ \ O}{\|\ \ \|}$$

with a catalyst to obtain said fluorinated ketone.

* * * * *